United States Patent [19]

Daniell et al.

[11] Patent Number: 5,680,108
[45] Date of Patent: Oct. 21, 1997

[54] APPARATUS AND METHOD FOR MONITORING A STEEPING BEVERAGE AND FOR INDICATING WHEN A DESIRED BEVERAGE STRENGTH IS ATTAINED

[76] Inventors: Anthony L. Daniell, 7355 Nita Ave., Canoga Park, Calif. 91303; Patrick J. Alger, P.O. Box 8674, Northridge, Calif. 91327

[21] Appl. No.: 629,119

[22] Filed: Apr. 8, 1996

[51] Int. Cl.$^6$ ............................ G08B 21/00
[52] U.S. Cl. .................... 340/603; 99/255; 250/215; 250/564; 250/573; 250/343; 340/540
[58] Field of Search ................... 340/603, 540; 99/285; 250/343, 564, 215, 573, 910

[56] References Cited

U.S. PATENT DOCUMENTS

| | | | |
|---|---|---|---|
| 2,278,767 | 4/1942 | Brophy | 250/215 |
| 4,644,855 | 2/1987 | Woolman et al. | 99/280 |
| 4,757,752 | 7/1988 | Robins et al. | 99/279 |
| 4,809,594 | 3/1989 | Vitous | 99/280 |
| 4,917,005 | 4/1990 | Knepler | 99/280 |
| 5,094,153 | 3/1992 | Helbling | 99/280 |
| 5,188,019 | 2/1993 | Vahabpour | 99/285 |
| 5,245,914 | 9/1993 | Vitous | 99/285 |
| 5,249,509 | 10/1993 | English | 99/285 |
| 5,369,398 | 11/1994 | Vancha | 99/285 |

Primary Examiner—Glen Swann
Attorney, Agent, or Firm—John J. Posta, Jr.

[57] ABSTRACT

A device and a related method of operation of the device for continuously monitoring the progress of a steeping beverage during the steeping process is disclosed which provides an indication to the user when the steeping beverage has reached an adjustable, desired level of steeping to thereby enable the making of a consistently steeped beverage without requiring the steeping operation to be timed or otherwise closely monitored. The device optically monitors the steeping beverage by using a photo diode to detect light from an LED which passes through a fixed measurement aperture immersed in the steeping beverage. By determining when the passage of light through the measurement aperture has decreased to a predetermined level indicative of both the color and the strength of the steeping beverage, an alarm may be provided to indicate that the beverage has steeped to precisely the strength desired.

22 Claims, 3 Drawing Sheets

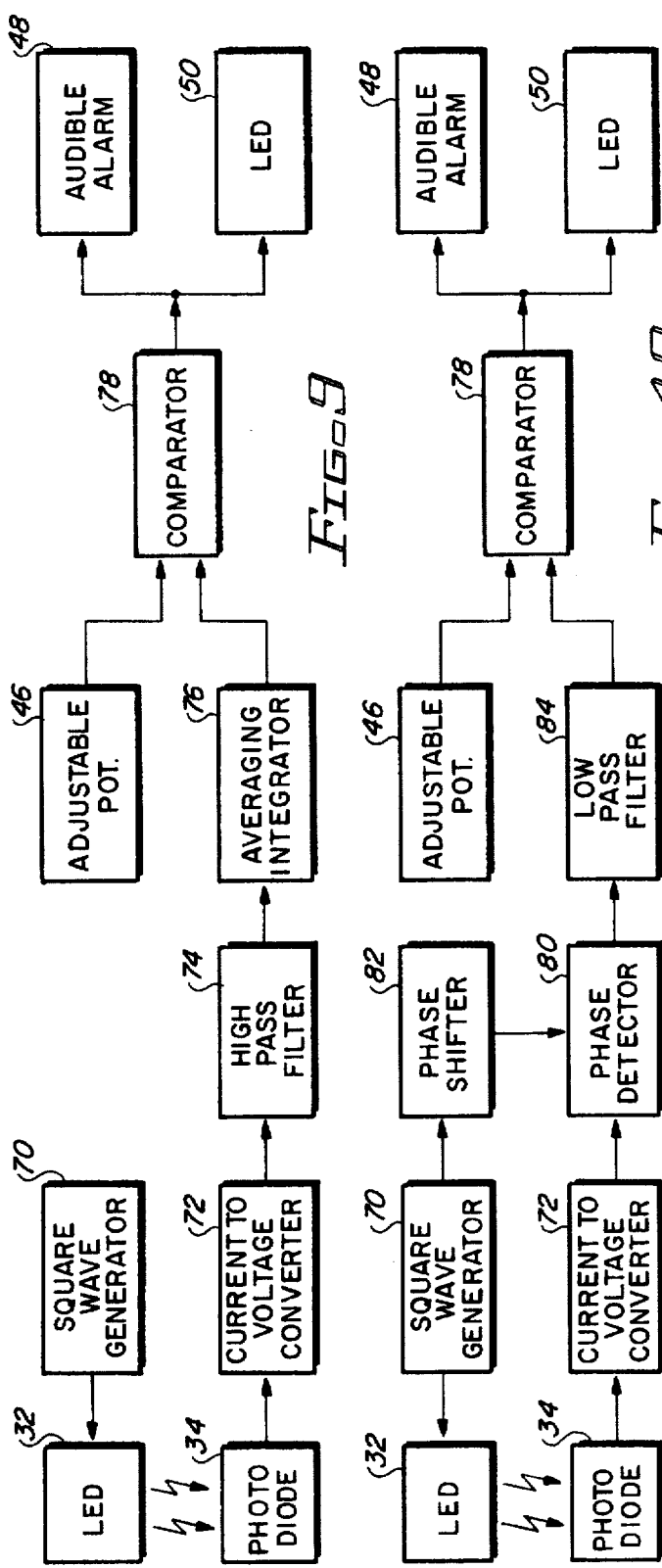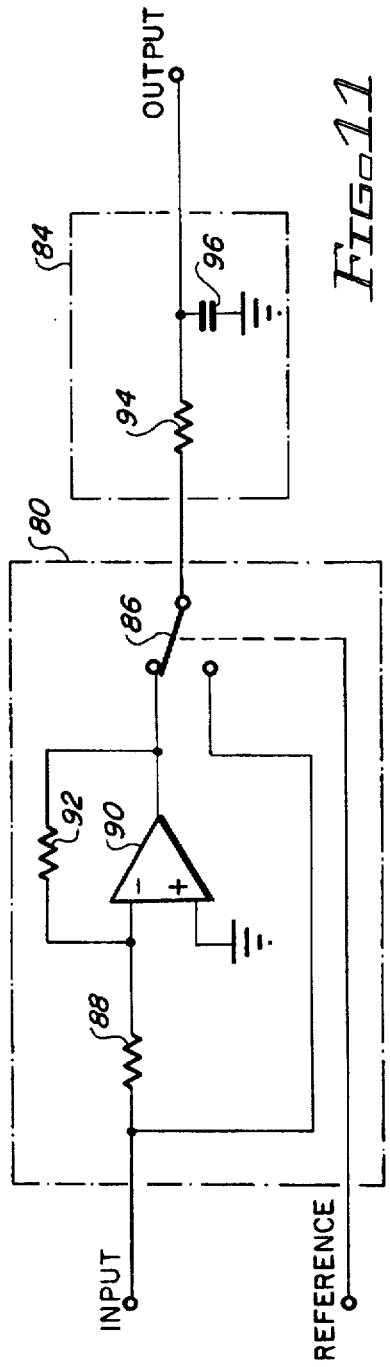

APPARATUS AND METHOD FOR MONITORING A STEEPING BEVERAGE AND FOR INDICATING WHEN A DESIRED BEVERAGE STRENGTH IS ATTAINED

BACKGROUND OF THE INVENTION

1. Field of the Invention

The present invention relates generally to the steeping of tea or like beverages, and more particularly to a device and a related method of operation of the device for continuously monitoring the progress of a steeping beverage during the steeping process, and for providing an indication to the user when the steeping beverage has reached an adjustable, desired level of steeping to thereby enable the making of a consistently steeped beverage without requiring the steeping operation to be timed or otherwise closely monitored.

Unlike the brewing of coffee, which is accomplished in a brewing process adjustable for the most part only by varying the amount of infusible material to be used, the steeping of hot tea for individual consumption is dependent on a number of different factors. The type and amount of the tea selected, the temperature of the water used, whether the tea is agitated in the hot water or not, and whether the tea is contained in a tea bag or in a small porous container such as a tea ball can all affect the time taken for the tea to steep to a desired strength. While keeping most of these factors constant will generally result in a relatively fixed time for the tea to reach a desired strength, all too often the tea is either too weak, thereby being bland and unsatisfying, or too strong, thereby presenting a bitterness or acidity which is unpleasant to the tongue.

As might be expected, human ingenuity has addressed a variety of problems incident to the brewing of various beverages, both hot and cold, and presents a number of ideas which may be considered. Coffee-type brewing devices have become quite popular. U.S. Pat. No. 4,917,005, to Knepler, illustrates one such device, with a feature designed to ensure that the temperature of the water is sufficiently hot before brewing can occur. U.S. Pat. Nos. 5,080,008 and 5,094,153, both to Helbling, illustrate just how sophisticated such devices have become, with a microprocessor being used to ensure that the brewed beverage is placed in an appropriately marked carafe. Unfortunately, while such devices work quite well to brew coffee, they are not capable of properly steeping tea suitable for the palates of most individuals.

A number of references illustrate improved devices for brewing iced tea. U.S. Pat. No. 4,757,752, to Ribins et al., U.S. Pat. No. 4,809,594, to Vitous, U.S. Pat. No. 5,188,019, to Vahabpour, and U.S. Pat. No. 5,245,914, to Vitous all teach iced tea brewing devices which produce a strong, concentrated infusate which is then mixed with cold water to produce the finished beverage. While such devices work quite well in the production of iced tea, hot tea is really a different beverage, and one in which small variations in the brewing process are much more apparent. None of these devices provide sufficient adjustment in the brewing process to suitably refine the resulting hot tea.

U.S. Pat. No. 4,644,855, to Woolman et al., teaches a hot tea maker which is designed for use in a restaurant or other large-scale food service application. The Woolman et al. device teaches a complex brewing process in which multiple fluid injections into the infusible material, which may be either coffee or tea, are alternated with agitation induced in the brewing area by the use of compressed air or steam. While the Woolman et al. device is designed to produce a uniform quality hot beverage, it is entirely inapplicable to the task at hand—ensuring consistency in the desired steeping characteristics of tea while retaining at least a degree of variability to allow the cup of tea to be tailored to the palate of an individual.

The only reference currently known in the art to vary the strength of a cup of tea is illustrated in U.S. Pat. No. 5,249,509, to English. The English reference teaches the use of a brewing vessel which fits over a cup. A quantity of infusible material such as tea is contained in a filter within the brewing vessel, and hot water is then poured into the brewing vessel. The brewing vessel is adjustable to regulate the flow of hot water contained therein in a path bypassing the filter, directly into the cup.

In this way, by controlling the amount of hot water bypassing the infusible material, the degree of steeping can be controlled. The primary disadvantage to the English device is that the flow rate through the filter must be necessarily slow, in order to enable the maximum strength to be of a sufficiently high level. In addition, the English device requires prepackaged filters which contain the infusible material, which means that it will be inapplicable if the user has a particular type of tea which he or she wishes to steep. Thus, the English device, while representing an improvement over the other devices mentioned above, will not prove acceptable to most tea drinkers desiring to steep a particular type of tea.

It is accordingly the primary objective of the present invention that it accommodate the use of any type of tea, whether in tea bags or in small porous containers such as tea balls, and allow the user to precisely determine when the tea has steeped to a desired strength. It is a related objective of the present invention that the tea strength be adjustable to taste and to the type of tea being steeped, so that, once determined, successive cups may be steeped with precisely the same characteristics. It is a further objective of the present invention that it be equally applicable whether the tea is being steeped in a cup, in a tea pot, or in any other container.

It is yet another objective of the tea strength measurement device of the present invention that it be useable anywhere, and as such, that the device of the present invention be compact and portable to facilitate its use anywhere. It is an additional objective that the device and method of the present invention be simple to implement, and that they require no special skill or even particular attention other than merely to initiate their use. It is a still further objective of the tea strength measurement device of the present invention that it be unobtrusive when in use so as not to draw undue attention to its use.

The tea strength measurement device of the present invention must also be of construction which is both durable and long lasting, and it should also require little or no maintenance to be provided by the user throughout its operating lifetime. In order to enhance the market appeal of the device of the present invention, it should also be of inexpensive construction to thereby afford it the broadest possible market. Finally, it is also an objective that all of the aforesaid advantages and objectives of the tea strength measurement device and method of the present invention be achieved without incurring any substantial relative disadvantage.

SUMMARY OF THE INVENTION

The disadvantages and limitations of the background art discussed above are overcome by the present invention.

Throughout the following discussions of the present invention, both in the summary and in the detailed description of the preferred embodiment of the present invention, it will be referred to as a tea strength measurement device. It will, however, be understood by those skilled in the art that the device and method of the present invention are equally applicable to broader use and may in fact be used to monitor the strength of any steeped beverage. Accordingly, it will be understood that while references herein are made to use of the present invention to monitor the strength of tea, this is in no way intended as a limitation of the application of the present invention, which may also determine the strength of other steeped beverages as well.

With this invention, a tea strength measurement device and a related method for the use thereof are taught which use the changing optical characteristics of the tea as it steeps to determine the progress of the steeping process. Since the color of the tea deepens as it steeps, by continuously monitoring the passage of light within a predetermined measurement aperture contained in the steeping tea, the optical characteristic may be thereby determined, and with it the instant strength of the steeping tea.

The tea strength measurement device of the present invention establishes a measurement aperture between a light source and a light detector. In the preferred embodiment of the present invention, the light source is a light emitting diode (LED), and the light detector is a photo diode. By mounting the LED and the photo diode to face each other in a fixed mechanical relationship (light emitted from the LED being directed onto the photo diode), the measurement aperture is thereby established. This measurement aperture will be located in the tea being steeped to determine the optical characteristic (the deepening color) of the tea as it steeps.

In order to minimize the effect of outside light on the determination of the optical characteristic in the measurement aperture, in the preferred embodiment the LED is driven by an oscillating signal. By determining only that portion of the signal detected by the photo diode which results from the oscillating signal, the optical characteristic within the measurement aperture may be determined irrespective of the amount of external light incident on the measurement aperture. Thus, it will be appreciated by those skilled in the art that as tea steeps within the measurement aperture, it deepens in color, causing less and less of the signal from the LED to reach the photo diode.

By continuously monitoring the tea by immersing the measurement aperture in the tea as it steeps, the degree of steeping of the tea may be continuously determined. By stopping the steeping process when the tea strength measurement device of the present invention indicates that the tea has reached the desired deepness of color, a perfect cup of tea may be steeped each and every time. By monitoring the level of the signal from the LED which is detected by the photo diode, which will steadily diminish as the tea steeps and deepens in color, the device can be made to provide an output signal when the signal diminishes to a preselected point, which preselected point is variable to allow for different types of teas and differing tastes as to the strength of the tea. The alarm provided may be audible or visual, or, in the preferred embodiment, both audible and visual.

The tea strength measurement device of the present invention may be implemented in either of two different devices. In a first embodiment, the tea strength measurement device may be built into a cup. In this embodiment, the LED and the photo diode are located within the cup in a spaced-apart relationship defining the measurement aperture. The control circuitry, batteries, controls, and audible and visual indicators may be built into the handle of the cup.

In a second embodiment, the tea strength measurement device may be embodied in an elongated housing member having a longitudinal slot located therein adjacent one end thereof. The longitudinal slot defines the measurement aperture, and the LED is mounted at one end of the longitudinal slot while the photo diode is located at the other end thereof. The controls and audible and visual indicators may be located at the end of the elongated housing member opposite the longitudinal slot, with batteries located inside the elongated housing member. By placing the end of the device having the longitudinal slot located therein into a cup of tea as it is being steeped, the tea strength measurement device can continuously monitor the steeping process.

It may therefore be seen that the present invention teaches a tea strength measurement device and method for use thereof which have application with any type of tea, whether in tea bags or in small porous containers such as tea balls, and which allow the user to precisely determine when the tea has steeped to a desired strength. The tea strength measurement device of the present invention allows the desired tea strength to be adjusted to taste and to the type of tea being steeped; once determined, successive cups may be steeped with precisely the same characteristic. The tea strength measurement device of the present invention is useable irrespective of whether the tea is being steeped in a cup, in a tea pot, or in a container having any size and configuration whatsoever.

The tea strength measurement device of the present invention is compact and portable to facilitate its use anywhere. It is simple to operate, and requires no special skill or even particular attention other than merely to initiate its use. The tea strength measurement device of the present invention is unobtrusive when in use so as not to draw undue attention to its use.

The tea strength measurement device of the present invention is also of construction which is both durable and long lasting, requiring little or no maintenance to be provided by the user throughout its operating lifetime. It is of inexpensive construction in order to enhance its market appeal and to thereby afford it the broadest possible market. Finally, all of the aforesaid advantages and objectives of the tea strength measurement device of the present invention are achieved without incurring any substantial relative disadvantage.

DESCRIPTION OF THE DRAWINGS

These and other advantages of the present invention are best understood with reference to the drawings, in which:

FIG. 9 is a functional schematic diagram showing a first embodiment of the control circuitry used in the operation of the tea strength measurement device of the present invention, using a high pass filter and an integrator;

FIG. 10 is a functional schematic diagram showing a second embodiment of the control circuitry used in the operation of the tea strength measurement device of the present invention, using a phase detector; and FIG. 11 is a schematic diagram of a phase detector which may be used in conjunction with the control circuitry illustrated functionally in FIG. 10.

DETAILED DESCRIPTION OF THE PREFERRED EMBODIMENT

The preferred embodiment of the present invention continuously monitors the optical characteristics of steeping tea by using an LED and a photo diode which are spaced apart on opposite sides of a fixed measurement aperture. By driving the LED with an oscillating signal and then determining the portion of the signal detected by the photo diode which is attributable to the oscillating signal, the color of the steeping tea may be monitored until it deepens to a preselected hue, at which time an alarm is initiated. In a first embodiment illustrated in FIGS. 1 through 5, the tea strength measurement device is installed in a cup, while in a second embodiment illustrated in FIGS. 6 through 8, the tea strength measurement device is measured in a thin, elongated housing member.

Figure 1:
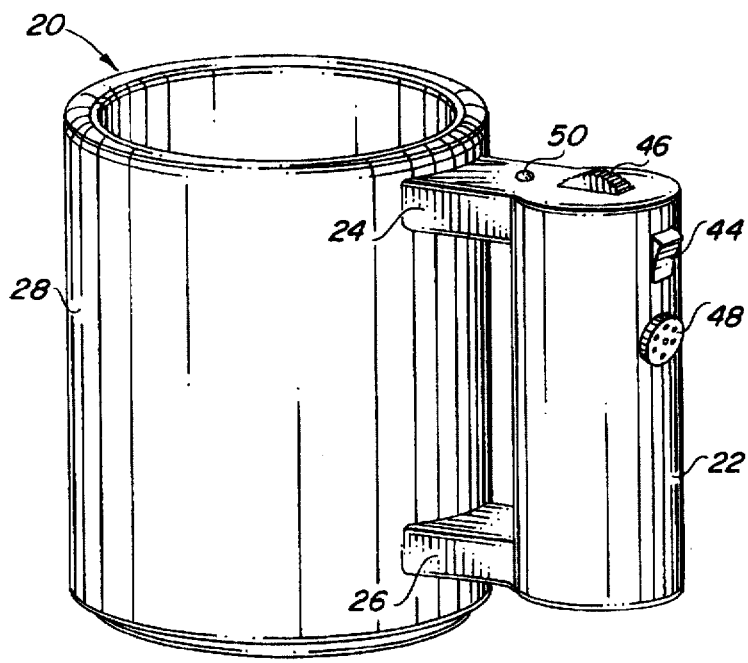
FIG. 1 is a perspective view of a first embodiment of the present invention, which is a cup having the tea strength measurement device of the present invention built into it, showing the controls and the audible and visual indicators.

Referring first to FIG. 1, a cup 20 is illustrated which has a handle 22 mounted on the side of the cup 20 by two leg members 24 and 26, as is conventional. The handle 22 and the leg members 24 and 26 together form a U, with the handle 22 being the base of the U and the leg members 24 and 26 being the legs of the U. The leg member 24 is attached to the cup 20 near the top of the cup 20, while the leg member 26 is attached to the cup 20 near the bottom of the cup 20. The cup 20 itself consists of a cylindrical wall member 28 and a bottom member 30.

Figure 2:
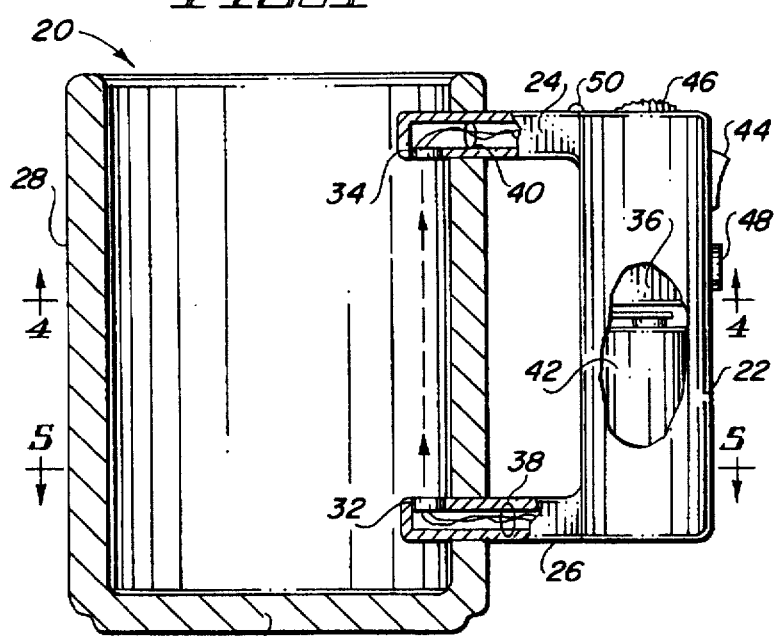
FIG. 2 is a cutaway view of the cup illustrated in FIG. 1, showing the locations and orientations of the LED and the photo diode within the cup, and also having a portion of the handle cut away to show a battery and control circuitry located therein.
Figure 3:
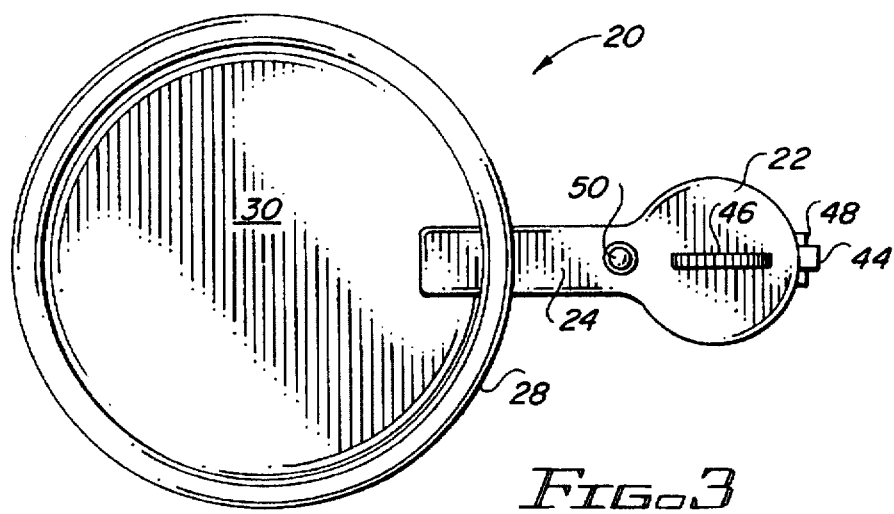
FIG. 3 is a top plan view of the cup illustrated in FIGS. 1 and 2.
Figure 4:
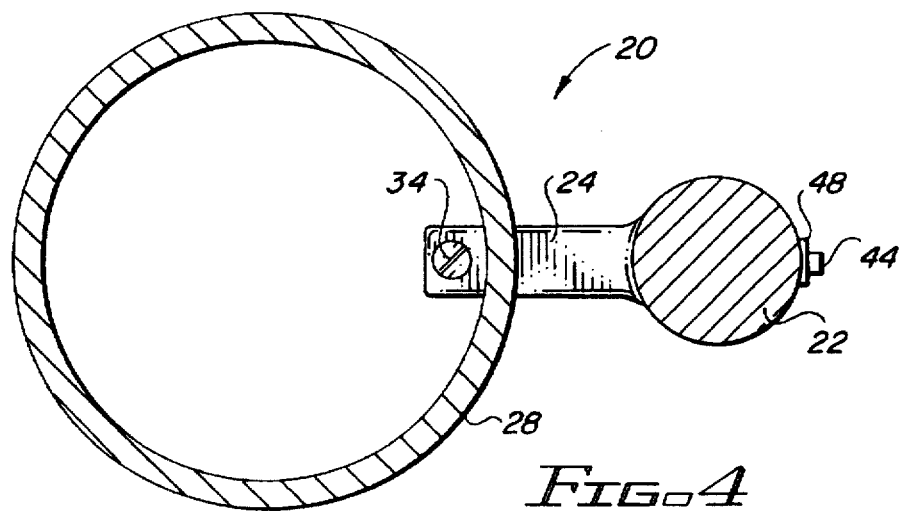
FIG. 4 is a first cross-sectional view of the cup illustrated in FIGS. 1 through 3, showing how the structure in which the photo diode is mounted in extends into the cup.
Figure 5:
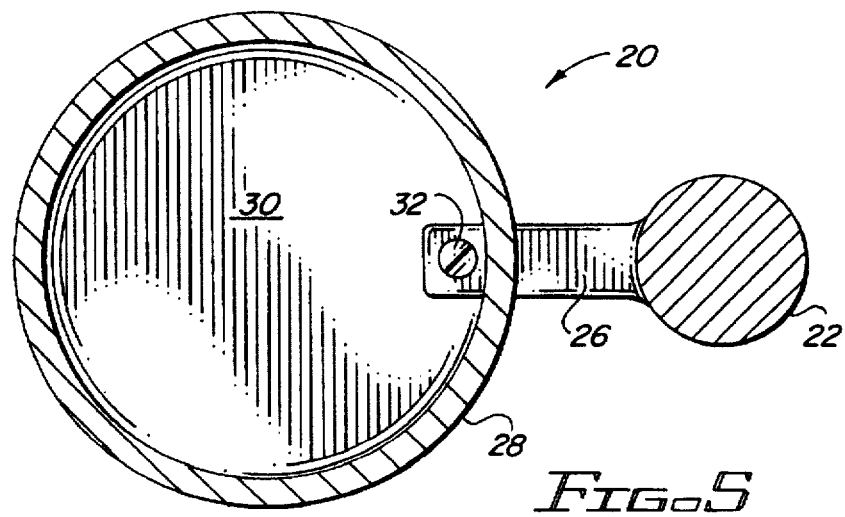
FIG. 5 is a second cross-sectional view of the cup illustrated in FIGS. 1 through 4, showing how the structure in which the LED is mounted in extends into the cup.

The leg member 24 extends through the cylindrical wall member 28 of the cup 20 and slightly into the interior of the cup 20, as best illustrated in FIGS. 2, 3, and 4. Similarly, the leg member 26 also extends through the cylindrical wall member 28 of the cup 20 into the interior of the cup 20, as best illustrated in FIGS. 2 and 5. The leg member 24 is located vertically directly above the leg member 26, as best shown in FIGS. 1 and 2.

Referring now to FIGS. 2 and 5, a light emitting diode (LED) 32 is located in the portion of the leg member 26 which extends into the interior of the cup 20 past the interior of the cylindrical wall member 28. The LED 32 is mounted so as to direct light emitted therefrom directly upward onto the bottom of the leg member 24. The LED 32 is also mounted in the leg member 26 in a sealed manner so as to be impervious to liquids in the cup 20.

Referring next to FIGS. 2 and 4, a photo diode 34 is located in the portion of the leg member 24 which extends into the interior of the cup 20 past the interior of the cylindrical wall member 28. The photo diode 34 is mounted so as to face directly downward toward the LED 32 mounted in the leg member 26, to thereby receive the maximum amount of light emitted from the LED 32 thereupon. The photo diode 34 is also mounted in the leg member 24 in a sealed manner so as to be impervious to liquids in the cup 20.

Referring now particularly to FIG. 2, mounted in the handle 22 is control circuitry 36, which is used to control the operation of the tea strength measurement device. Wires 38 are used to connect the LED 32 with the control circuitry 36, and wires 40 are used to connect the photo diode 34 with the control circuitry 36. Also mounted in the handle 22 is a battery 42 which is used to power the tea strength measurement device.

Referring now to FIGS. 1, 2, and 3, the controls of the tea strength measurement device are illustrated as being mounted in the handle 22. An on/off switch 44 which is used to turn power to the tea strength measurement device on and off is mounted in the handle 22 on the side near the top thereof. A threshold adjustment potentiometer 46 used to adjust the degree of opaqueness (which increases with increasing strength of tea being steeped in the cup 20) which will be required for the tea strength measurement device to signal that the tea has been steeped to the desired strength is mounted in the top of the handle 22.

In the preferred embodiment, both an audible alarm and a visual alarm are provided to indicate when the tea has been steeped to the desired strength. It should be noted that either alarm could also be used exclusively if desired. An audible alarm speaker 48 is mounted in the side of the handle 22 below the on/off switch 44. A visual alarm LED 50 is mounted in the top of the leg member 24 near its point of attachment to the handle 22. The operation of the tea strength measurement device illustrated in FIGS. 1 through 5 (and of the alternate embodiment described immediately below in conjunction with FIGS. 6 through 8) will be discussed below in conjunction with the discussion of FIGS. 9 through 11.

Figure 6:
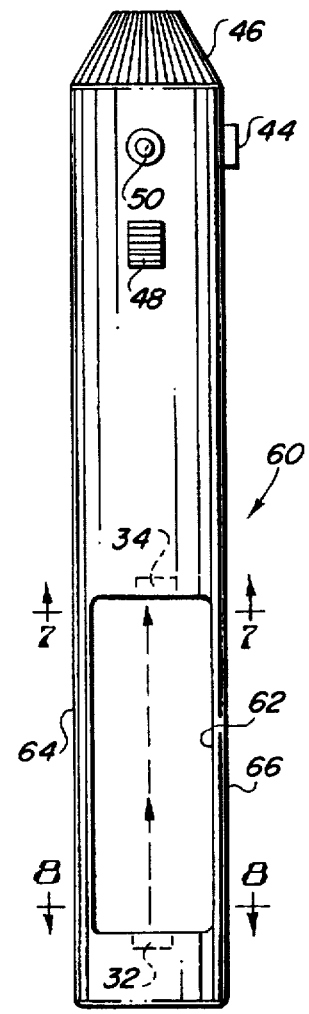
FIG. 6 is a side plan view of a second embodiment of the present invention, which is an elongated device having the tea strength measurement device of the present invention built into it, showing an elongated longitudinal slot defining a measurement aperture located at one end of the device, and showing the controls and the audible and visual indicators located at the other end of the device.
Figure 7:
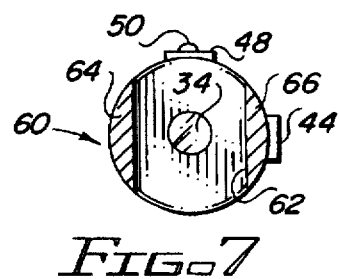
FIG. 7 is a first cross-sectional view of the device illustrated in FIG. 6, showing the location of the photo diode at one end of the longitudinal slot.
Figure 8:
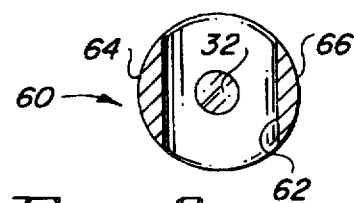
FIG. 8 is a second cross-sectional view of the device illustrated in FIGS. 6 and 7, showing the location of the LED at the other end of the longitudinal slot.

Referring now to FIGS. 6 through 8, an alternate embodiment tea strength measurement device is illustrated. While the tea strength measurement device illustrated in FIGS. 1 through 5 comprises a cup in which tea may be steeped, the tea strength measurement device illustrated in FIGS. 6 through 8 is an elongated device which may be placed into a cup, pot, or other container in which tea is being steeped.

Functionally, the tea strength measurement device illustrated in FIGS. 6 through 8 operates in the same manner and includes the same components as the tea strength measurement device illustrated in FIGS. 1 through 5. As such, the various identical components of the tea strength measurement device illustrated in FIGS. 6 through 8 are given the same numerical indicia as they were given in the tea strength measurement device illustrated in FIGS. 1 through 5.

Referring now particularly to FIG. 6, the device is housed in an elongated housing member 60 which is essentially cylindrical in configuration. The elongated housing member 60 has an elongated longitudinal slot 62 located therein near the bottom as illustrated. The elongated longitudinal slot 62 extends through the elongated housing member 60, and is defined between two opposed side walls 64 and 66.

Referring now to FIGS. 6 and 8, the light emitting diode (LED) 32 is located in the elongated housing member 60 at the bottom of the elongated longitudinal slot 62. The LED 32 is mounted in the elongated housing member 60 so as to direct light emitted therefrom directly upward toward the top of the elongated longitudinal slot 62 in the portion of the elongated housing member 60. The LED 32 is also mounted in the elongated housing member 60 in a sealed manner so as to be impervious to liquid.

Referring next to FIGS. 6 and 7, the photo diode 34 is located in the elongated housing member 60 at the top of the elongated longitudinal slot 62. The photo diode 34 is mounted so as to face directly downward toward the LED 32 mounted at the bottom of the elongated longitudinal slot 62, to thereby receive the maximum amount of light emitted from the LED 32. The photo diode 34 is also mounted in the elongated housing member 60 in a sealed manner so as to be impervious to liquid.

Referring now particularly to FIG. 6, the on/off switch 44 is mounted in the elongated housing member 60 on the side near the top thereof. The threshold adjustment potentiometer 46 is mounted in the top of the elongated housing member 60. The audible alarm speaker 48 is mounted in the side of the elongated housing member 60. The visual alarm LED 50 is mounted in the side of the elongated housing member 60 just above the audible alarm speaker 48.

Although not specifically illustrated in FIGS. 6 through 8, it will at once be understood by those skilled in the art that the tea strength measurement device illustrated therein also includes the control circuitry 36, the wires 38 from the LED 32 to the control circuitry 36, the wires 40 from the photo diode 34 to the control circuitry 36, and the battery 42 (all shown in FIG. 2).

Referring next to FIG. 9, a functional schematic diagram showing a first embodiment of the control circuitry which may be used in the operation of both of the tea strength measurement devices of the present invention previously discussed is illustrated. Several of the components of the tea strength measurement devices illustrated above are given the same numerical indicia as they were given previously.

A square wave generator 70 is used to drive the LED 32 in order to produce a "chopped" light signal from the LED 32. The square wave generator 70 operates at a sufficiently high frequency to allow the system to discriminate against ambient light which may be detected by the photo diode 34. The measurement aperture is the area between the LED 32 and the photo diode 34, and is normally immersed in steeping tea.

The signal received by the photo diode 34 is converted into a voltage by a current to voltage converter 72. The signal is then supplied to a high pass filter 74, which will reject the portion of the signal due to ambient light and will pass the portion of the signal due to the chopped light from the LED 32. The signal from the high pass filter 74 is then time integrated in an averaging integrator 76 to produce an output which is the time-average of the signal from the high pass filter 74.

The output from the averaging integrator 76 is then supplied to a comparator 78, where it is compared to a threshold set by the threshold adjustment potentiometer 46. When the signal from the averaging integrator 76 drops below the signal set by the threshold adjustment potentiometer 46, a trigger signal will be sent by the comparator 78 to the audible alarm speaker 48 and the visual alarm LED 50.

Referring now to FIG. 10, a functional schematic diagram showing a second embodiment of the control circuitry which may be used in the operation of both of the tea strength measurement devices of the present invention previously discussed is illustrated. Again, several of the components of the tea strength measurement device illustrated above are given the same numerical indicia as they were given previously.

The square wave generator 70 is again used to drive the LED 32 in order to produce a "chopped" light signal from the LED 32. The square wave generator 70 again operates at a sufficiently high frequency to allow the system to discriminate against ambient light which may be detected by the photo diode 34. The measurement aperture is once again the area between the LED 32 and the photo diode 34, and is again normally immersed in steeping tea.

The signal received by the photo diode 34 is again converted into a voltage by a current to voltage converter 72. The signal is then supplied to a phase detector 80, which is the first of three components comprising what is known collectively as a "lock-in detection" apparatus. The reference signal from the square wave generator 70 is supplied to a phase shifter 82, which is the second component of the lock-in detection apparatus. The output of the phase shifter 82 is also supplied as an input to the phase detector 80.

The output of the phase detector 80 is supplied to a low pass filter 84, which is the last of the components comprising the lock-in detection apparatus. The operation of the lock-in detection apparatus may be illustrated with reference to FIG. 11, which shows an exemplary schematic for the phase detector 80 and the low pass filter 84. The phase detector 80 may be thought of as a unity gain linear amplifier whose gain is cyclically alternated between positive and negative unity gain by a reference signal controlling a FET switch 86.

One side of a first resistor 88 is connected to the input signal to the phase detector 80, with the other side of the first resistor 88 being connected to the inverting input of an op amp 90. One side of a second resistor 92 is also connected to the inverting input of an op amp 90, with the other side of the second resistor 92 being connected to the output of the op amp 90. The non-inverting input of the op amp 90 is grounded. The first and second resistors 88 and 92 may be, for example, 10K Ohm resistors, so that the output of the op amp 90 will be an inversion of the signal supplied as an input to the phase detector 80.

The output of the FET switch 86, which is also the output of the phase detector 80, will thus be switched between the signal supplied as an input to the phase detector 80 and an inversion of the signal supplied as an input to the phase detector 80. The reference signal which is used to control the FET switch 86 is the output from the phase shifter 82 (FIG. 10).

The low pass filter 84 is a simple RC filter consisting of a third resistor 94 and a capacitor 96. One side of the third resistor 94 is connected to the output of the phase detector 80, with the other side of the third resistor 94 being the output of the low pass filter 84. One side of the capacitor 96 is also connected to the output of the low pass filter 84 (the other side of the third resistor 94), while the other side of the capacitor 96 is grounded.

Referring once again to FIG. 10, the phase shifter 82 is used to shift the phase of the square wave generated by the square wave generator 70 prior to supplying it to the phase detector 80. The phase shifter 82 is adjusted at the time of manufacture of the tea strength measurement device to produce the maximum output from the low pass filter 84 when there is no obstruction (i.e., no liquid) in the measurement aperture between the LED 32 and the photo diode 34. The lock-in detection apparatus provides for a high degree of rejection of interfering light sources from ambient lighting.

The output from the low pass filter 84 is then supplied to the comparator 78, where it is compared to the threshold set by the threshold adjustment potentiometer 46. When the signal from the low pass filter 84 drops below the signal set by the threshold adjustment potentiometer 46, a trigger signal will be sent by the comparator 78 to the audible alarm speaker 48 and the visual alarm LED 50.

The operation of the tea strength measurement devices illustrated in FIGS. 1 through 5 will now be discussed. Hot water is poured into the cup 20, and a tea bag is then placed into the cup (away from the measurement aperture between the LED 32 and the photo diode 34). As the tea steeps, it will deepen in color, decreasing the amount of light from the LED 32 which is passed to and detected by the photo diode 34. By setting the alarm to be initiated when the tea steeps to the desired character (deepens to the desired color), the tea strength measurement device may be set to indicate when a cup of tea which is exactly of the strength desired by the person steeping the tea has been produced.

Similarly with respect to the tea strength measurement device illustrated in FIGS. 6 through 8, hot water is poured into a cup or tea pot, and a tea bag is then placed therein. The tea strength measurement device is placed into the cup or tea pot (with the tea bag again located away from the measurement aperture between the LED 32 and the photo diode 34). The rest of the operation of the tea strength measurement device illustrated in FIGS. 6 through 8 is identical to the opdevice illustrated strength measurement device illustrated in FIGS. 1 through 5.

Initial calibration of the tea strength measurement devices of the present invention is accomplished by turning the device on, and setting the threshold to a starting value, which is typically in the center of the range. A tea bag is then placed into hot water to begin steeping, and the tea bag is agitated in the hot water until the device sounds an alarm. The tea bag is then promptly removed, and the tea is sampled.

If the tea is too "watery," the strength setting will be increased (thereby decreasing the threshold) and the steeping process repeated with fresh hot water and another tea bag. Likewise, if the tea is too strong, the strength setting will be decreased (thereby increasing the threshold) and the steeping process repeated with fresh hot water and another tea bag. Once the desired tea taste is achieved, no further adjustment of the threshold adjustment potentiometer 46 will be required. Subsequent uses will produce tea at the same strength each and every time the tea strength measurement device of the present invention is used.

It may therefore be appreciated from the above detailed description of the preferred embodiment of the present invention that it teaches a tea strength measurement device and method for use thereof which have application with any type of tea, whether in tea bags or in small porous containers such as tea balls, and which allow the user to precisely determine when the tea has steeped to a desired strength. The tea strength measurement device of the present invention allows the desired tea strength to be adjusted to taste and to the type of tea being steeped; once determined, successive cups may be steeped with precisely the same characteristic. The tea strength measurement device of the present invention is useable irrespective of whether the tea is being steeped in a cup, in a tea pot, or in a container having any size and configuration whatsoever.

The tea strength measurement device of the present invention is compact and portable to facilitate its use anywhere. It is simple to operate, and requires no special skill or even particular attention other than merely to initiate its use. The tea strength measurement device of the present invention is unobtrusive when in use so as not to draw undue attention to its use.

The tea strength measurement device of the present invention is also of construction which is both durable and long lasting, requiring little or no maintenance to be provided by the user throughout its operating lifetime. It is of inexpensive construction in order to enhance its market appeal and to thereby afford it the broadest possible market. Finally, all of the aforesaid advantages and objectives of the tea strength measurement device of the present invention are achieved without incurring any substantial relative disadvantage.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A device for measuring the strength of tea or a like steeped beverage, comprising:

a light source;

means for detecting light generated by said light source and for producing a signal proportional to the amount of light from said light source which is detected;

a mounting member for supporting said light source and said light detecting means in a fixed, spaced-apart relationship with an open measurement aperture located therebetween, said light source and said light detecting means being relatively oriented toward each other such that light generated by said light source will fall directly upon said light detecting means, and such that the greatest possible amount of light generated by said light source will be detected by said light detecting means, said mounting member being adapted to be placed into tea as the tea is being steeped; and means for producing an alarm signal when said signal from said light detecting means reaches a predetermined, variable threshold value.

2. A device as defined in claim 1, wherein said light source comprises:

a light emitting diode (LED).

3. A device as defined in claim 2, wherein said light source additionally comprises:

means for driving said LED to produce a chopped light from said LED.

4. A device as defined in claim 3, wherein said means for driving said LED comprises:

a square wave generator.

5. A device as defined in claim 1, wherein said light detecting means comprises:

a photo diode for producing an electrical signal proportional to light detected by said photo diode; and means for discriminating between the portion of said electrical signal indicative of light generated by said light source and the portion of said electrical signal indicative of light other than that generated by said light source, said signal from said light detecting means comprising only the portion of said electrical signal indicative of light generated by said light source.

6. A device as defined in claim 5, wherein said electrical signal comprises an electrical current, and wherein said light detecting means additionally comprises:

a current to voltage converter for converting said electrical current into an electrical voltage signal.

7. A device as defined in claim 5, wherein said discriminating means comprises:

a high pass filter for filtering said electrical signal produced by said photo diode.

8. A device as defined in claim 7, wherein said discriminating means additionally comprises:

an averaging integrator for integrating the filtered electrical signal over a predetermined period of time and thereby producing an integrated output signal which is the time-average of the filtered electrical signal over said predetermined period of time.

9. A device as defined in claim 5, wherein said discriminating means comprises:

a lock-in detector.

10. A device as defined in claim 9, additionally comprising an oscillator producing an output to drive said light source, wherein said lock-in detector comprises:

a phase detector having as a first input said electrical signal produced by said photo diode, said phase detector producing an output signal;

a phase shifter for varying the phase of said output from said oscillator and providing it to said phase detector as a second input; and a low pass filter for filtering said output signal produced by said phase detector.

11. A device as defined in claim 10, wherein said oscillator comprises a square wave oscillator, and wherein said phase detector comprises:

a unity gain linear amplifier whose gain is cyclically alternated between positive and negative unity gain by said second input.

12. A device as defined in claim 10, additionally comprising:

means for adjusting the phase of said output from said oscillator provided to said phase detector as a second input to produce the maximum possible signal from said light detecting means when no obstruction is located in said measurement aperture.

13. A device as defined in claim 1, wherein said mounting member comprises:

a cup, said light source and said light detecting means being mounted inside said cup, said measurement aperture thereby being located within said cup, said cup for containing tea as the tea is being steeped.

14. A device as defined in claim 1, wherein said mounting member comprises:

an elongated housing member having an elongated longitudinal slot located therein near one end thereof, saidlight source being located at one end of said elongated longitudinal slot and said light detecting means being located at the other end of said elongated longitudinal slot, said elongated longitudinal slot comprising said measurement aperture, said one end of said elongated housing member being for placement into tea as the tea is being steeped.

15. A device as defined in claim 1, wherein said means for producing an alarm signal comprises:

means for setting said threshold value; and means for determining when said signal from said light detecting means reaches said threshold value.

16. A device as defined in claim 15, wherein said means for setting said threshold value comprises:

a potentiometer.

17. A device as defined in claim 15, wherein said means for determining when said signal from said light detecting means reaches said threshold value comprises:

a comparator.

18. A device as defined in claim 15 wherein said means for producing an alarm signal additionally comprises:

means for producing an audible alarm.

19. A device as defined in claim 15 wherein said means for producing an alarm signal additionally comprises:

means for producing a visual alarm.

20. A device for measuring the strength of tea or a like steeped beverage, comprising:

a light emitting diode (LED);

a photo diode for producing an electrical current signal proportional to light detected by said photo diode;

a current to voltage converter for converting said electrical current signal into an electrical voltage signal means for discriminating between the portion of said electrical voltage signal indicative of light generated by said LED and the portion of said electrical voltage signal indicative of light other than that generated by said LED, said discriminating means producing a signal comprising only, and proportional to, the portion of said electrical voltage signal indicative of light generated by said LED;

a mounting member for supporting said LED and said photo diode in a fixed, spaced-apart relationship with an open measurement aperture located therebetween, said LED and said photo diode being relatively oriented toward each other such that light generated by said LED will fall directly upon said photo diode, and such that the greatest possible amount of light generated by said LED will be detected by said photo diode, said mounting member being adapted to be placed into tea as the tea is being steeped;

means for setting a threshold value; and means for determining when said signal from said discriminating means reaches said threshold value and for producing an alarm signal in response thereto, indicating that the tea being steeped has reached a desired strength.

21. A device for measuring the strength of tea or a like steeped beverage, comprising:

a light source;

means for detecting light generated by said light source and for producing a signal proportional thereto;

a mounting member for supporting said light source and said light detecting means in a fixed, spaced-apart relationship with an open measurement aperture located therebetween, said light source and said light detecting means being relatively oriented toward each other, said mounting member being adapted to be placed into tea as the tea is being steeped; and means for producing an alarm signal when said signal from said light detecting means reaches a threshold value.

22. A method for measuring the strength of tea or a like steeped beverage, comprising:

supporting a light source and a light detector in a fixed, spaced-apart relationship with an open measurement aperture located therebetween, said light source and said light detector being relatively oriented toward each other such that light generated by said light source will fall directly upon said light detector, and such that the greatest possible amount of light generated by said light source will be detected by said light detector, said mounting member being adapted to be placed into tea as the tea is being steeped;

detecting light generated by said light source with said light detector and producing a signal proportional to the amount of light from said light source which is detected by said light detector; and producing an alarm signal when said signal from said light detector reaches a predetermined, variable threshold value.

* * * * *